United States Patent
Le Huec et al.

(10) Patent No.: US 10,524,723 B2
(45) Date of Patent: Jan. 7, 2020

(54) METHOD FOR MEASURING THE DISPLACEMENTS OF A VERTEBRAL COLUMN

(71) Applicant: ALPHATEC SPINE, INC., Carlsbad, CA (US)

(72) Inventors: Jean-Charles Le Huec, Pessac (FR); Estelle Duveau, Grenoble (FR); Sylvain Besson, Villard Bonnot (FR); Philippe Augerat, Saint-Ismier (FR)

(73) Assignee: ALPHATEC SPINE, INC., Carlsbad, CA (US)

( * ) Notice: Subject to any disclaimer, the term of this patent is extended or adjusted under 35 U.S.C. 154(b) by 562 days.

(21) Appl. No.: 14/338,951

(22) Filed: Jul. 23, 2014

(65) Prior Publication Data
US 2016/0022176 A1    Jan. 28, 2016

(51) Int. Cl.
*A61B 5/00* (2006.01)
*A61B 5/107* (2006.01)
(Continued)

(52) U.S. Cl.
CPC ............ *A61B 5/4566* (2013.01); *A61B 5/068* (2013.01); *A61B 5/1071* (2013.01); *A61B 5/1121* (2013.01); *A61B 5/1127* (2013.01); *A61B 6/12* (2013.01); *A61B 6/461* (2013.01); *A61B 6/505* (2013.01); *A61B 6/5217* (2013.01); *A61B 17/1757* (2013.01); *A61B 17/70* (2013.01); *A61B 17/7002* (2013.01); *A61B 2034/2068* (2016.02); *A61B 2090/067* (2016.02); *A61B 2090/3966* (2016.02)

(58) Field of Classification Search
CPC ....................................................... A61B 6/00
See application file for complete search history.

(56) References Cited

U.S. PATENT DOCUMENTS

| 6,190,320 B1 | 2/2001 | Lelong |
| 6,226,548 B1 * | 5/2001 | Foley ................. A61B 17/7083 600/426 |

(Continued)

FOREIGN PATENT DOCUMENTS

| EP | 1 442 715 A2 | 8/2004 |
| EP | 1 523 950 A1 | 4/2005 |

(Continued)

*Primary Examiner* — James M Kish
(74) *Attorney, Agent, or Firm* — Oliff PLC

(57) ABSTRACT

A method for measuring the displacements of a vertebral column, a vertebra of the column including a location marker attached thereto and providing a location system with an orientation of the location marker, the method including: a detection of an initial orientation of the location marker associated with a vertebra, a determination of an initial orientation of a vertebral plane parallel to at least one end plate of the vertebra, and a calculation of a geometric transformation associated with the vertebra correlating the initial orientation of the vertebral plane with the initial orientation of the location marker, a detection of the current orientation of the location marker, and a calculation of the current orientation of the vertebral plane of the vertebra from the current orientation of the location marker and the geometrical transformation associated with the vertebra.

22 Claims, 9 Drawing Sheets

(51) Int. Cl.
  *A61B 5/06* (2006.01)
  *A61B 5/11* (2006.01)
  *A61B 6/12* (2006.01)
  *A61B 6/00* (2006.01)
  *A61B 17/70* (2006.01)
  *A61B 17/17* (2006.01)
  *A61B 34/20* (2016.01)
  *A61B 90/00* (2016.01)

(56) References Cited

U.S. PATENT DOCUMENTS

| | | |
|---|---|---|
| 6,519,319 B1 | 2/2003 | Marino et al. |
| 2002/0087101 A1* | 7/2002 | Barrick .............. A61B 5/1077 600/587 |
| 2003/0130576 A1 | 7/2003 | Seeley et al. |
| 2005/0096535 A1 | 5/2005 | de la Barrera |
| 2005/0119593 A1 | 6/2005 | Gallard et al. |
| 2006/0085072 A1* | 4/2006 | Funk .............. A61F 2/4405 623/17.11 |
| 2008/0208055 A1 | 8/2008 | Bertram et al. |
| 2010/0030232 A1* | 2/2010 | Zehavi .............. A61B 34/10 606/130 |
| 2010/0121153 A1* | 5/2010 | To .............. A61B 10/06 600/214 |
| 2011/0157230 A1 | 6/2011 | Davydov |
| 2012/0172700 A1* | 7/2012 | Krishnan .............. A61B 6/032 600/407 |
| 2013/0060146 A1* | 3/2013 | Yang .............. A61B 5/055 600/476 |
| 2013/0268007 A1 | 10/2013 | Rezach et al. |
| 2014/0121676 A1* | 5/2014 | Kostrzewski .......... A61B 19/26 606/130 |
| 2014/0323845 A1* | 10/2014 | Forsberg .............. A61B 5/4561 600/407 |

FOREIGN PATENT DOCUMENTS

| | | |
|---|---|---|
| WO | WO 03/073946 A1 | 9/2003 |
| WO | WO 2005/084131 A2 | 9/2005 |
| WO | 2007/085085 A1 | 8/2007 |
| WO | 2007/121337 A2 | 10/2007 |
| WO | 2008/079546 A2 | 7/2008 |
| WO | 2013/044157 A1 | 3/2013 |

* cited by examiner

METHOD FOR MEASURING THE DISPLACEMENTS OF A VERTEBRAL COLUMN

TECHNICAL FIELD OF THE INVENTION

The invention relates to the measurement of the displacements of a vertebral column.

STATE OF THE ART

Currently, x-ray images are used to measure the curvature of the vertebral column of a patient. During a surgical operation the curvature of the vertebral column can be modified in order to reduce natural deformations or those occurred due to a trauma. In general, a surgeon takes two x-ray pictures, a front one and a side one, before the surgical operation in order to determine a distortion, and two X-ray pictures after the surgical operation in order to check the reduction of the deformation. However, during the surgical operation, the surgeon visually evaluates the correction of the curvature, but she/he does not have means for making a real-time check of the displacements of the vertebrae in the vertebral column.

U.S. patent application US20050096535 can be mentioned which discloses a method for recording two-dimensional pictures of digital markers obtained during a knee surgery, comprising the steps of:

importing two-dimensional X-ray pictures of the patient into a memory of a surgical navigation system capable of determining the position and orientation of an object;

digitizing markers;

determining the position of an axis of the leg with the help of the digitized markers;

recording a two-dimensional picture of the axis and displaying the recorded picture; and guiding the positioning of a cutting template inside the knee joint by using the navigation system with the help of the markers, the cutting template being meant to be placed at the end of the femur in order to shape the bone for receiving an implant.

In addition, the navigation system can calculate a plane passing through the center of the tibia, the medial malleolus and the lateral malleolus of the ankle, in order to determine an interest axis of the tibia. The imported picture of the patient and the recorded picture of the axis are displayed in the left corner of the display panel. However, the navigation system is not adapted for measuring a displacement of the vertebrae in a vertebral column, as it requires an access to the femoral surface, which is not necessarily the case of a vertebral column surgery during which an access to the surface of the vertebra is not possible.

U.S. patent application US20130268007 discloses a method for measuring an angle of a spinal implant, in particular a rod for linking vertebrae, comprising the use of a probe configured for measuring an angle in a measurement plane (the sagittal plane). The probe can include an accelerometer and magnetic sensors for measuring the angle. The probe is placed onto the implant, the probe having an end configured so as to fit the shape of the implant. But the system measures angles of the implant, it does not allow to measure the displacement of the body of a vertebra. There is no real-time check.

International application WO03073946 discloses a method for controlling the balance of a vertebral column, wherein:

the relative three-dimensional position of the vertebrae is determined by means of digital anatomical points on X-ray pictures;

the position of the spinal segments is determined; and a vertebral imbalance is displayed or not.

For each vertebra at least four points are identified in order to reproduce the vertebral body, at least three points are identified for the sacrum in order to form a triangle. Then the digitized points are incorporated into the X-ray pictures. For example, a touch probe provided with a location marker is used to rebuild a virtual space of the outer outline of the surface of the posterior arch of the vertebra. But it provides only a two-dimensional information, which is not sufficiently accurate for a vertebral column surgery. Furthermore, it does not allow to determine the displacement of the vertebral bodies in real time.

U.S. patent application US20030130576 discloses a surgical imaging system for displaying a picture containing an indication of the position of an instrument, and a picture of a patient, and comprising a processor for displaying both pictures for a navigation during a surgery. Said system uses an X-ray apparatus, such as a fluoroscope, and a marker fixed to a surgical tool, such as a probe. But the document relates to a process for guiding an instrument on an X-ray picture, it does not measure a relative position of a bone with respect to the other, or the displacement of the vertebral bodies of the patient.

International Application WO2005084131 discloses an apparatus for measuring the inclination of an object, such as an inclinometer. The inclination of the vertebral column is detected by an electromagnetic field probe detecting the spinous process of each vertebra. The handling principle consists in holding the measuring device with one hand and in maintaining it perpendicular to the patient's back. Initially, a semi-circular arch of the device is positioned above the spinal process of the seventh cervical vertebra. Then the device is moved along the vertebral column down to the first sacral vertebra. The probe acquires several pictures per vertebra. A tracker coupled to the probe can also be used, and the probe measures the position and inclination of the tracker which is moved along the vertebral column. In addition, the apparatus may comprise markers cooperating with a three-dimensional optical navigation system for identifying and calculating the angles of inclination of the vertebrae. However, the measuring apparatus cannot determine the deformation of the vertebral column in real time, because the apparatus must be moved along the vertebral column in order to perform the measurement of the inclination of the vertebrae.

U.S. patent application US20080208055 discloses a method for aligning fragments of a fractured bone. The method uses an ultrasonic apparatus equipped with a location marker and location markers positioned on each fragment. The ultrasonic apparatus can detect characteristic points of reference on the circumference of the bone fragments. In this method, a spatial position and/or orientation of each marker is determined, and an alignment is determined from the positions determined with respect to a particular criterion. But an ultrasound imaging process is not very accurate and cannot define a specific profile of an anatomical structure.

U.S. Pat. No. 6,190,320 discloses a picture processing method, comprising:

an acquisition, with the help of an ultrasonic transducer coupled to an echographic device, of a digital echographic picture of a structure that is non-transparent for ultrasonic waves; and an extraction of the outlines of the structure.

However, the system requires complex picture processing algorithms for extracting the outlines of a vertebra. In addition, the measurement is not very accurate because it is made from ultrasonic echographic pictures requiring the use of a preoperative picture having a high definition.

U.S. Pat. No. 6,519,319 discloses a reticle for a picture detector comprising a flat radio-transparent portion, a pair of first marks arranged on the surface of the flat portion, and a second mark arranged on the surface of the flat portion in order to indicate the center of the reticle. The reticle allows to align the detector with an intervertebral plane of the vertebral column of the patient. In addition, the reticle allows to guide a surgical instrument. But it uses a specific reticle on the detector which requires to guide the surgical tool in a single plane, which makes it impossible to measure the displacement of a vertebra in all directions.

Patent application US20110157230 discloses means for determining the measure of relative positions and dimensions of vertebrae, with respect to each other, from flat X-ray pictures. The method allows to determine the representative corners of a vertebral body. But it provides only a two-dimensional and not real-time information, which is not sufficiently accurate for a vertebral column surgery.

OBJECT OF THE INVENTION

An object of the invention is to overcome the above-mentioned disadvantages, and in particular to provide a method for measuring the displacements of the vertebrae of a vertebral column.

In one aspect of the invention, it is proposed a method for measuring the displacements of a vertebral column, the vertebral column having a segment comprising at least one vertebra, each vertebra in the segment having a body delimited by an upper vertebral end plate and a lower vertebral end plate, and each vertebra in the segment having a location marker associated, attached thereto and providing an orientation of the location marker in a global reference frame of a location system.

The method comprises:
an initial step, for each vertebra in the segment, comprising:
  a detection, in the global reference frame, of an initial orientation of the location marker associated with the vertebra in the segment,
  a determination, in the global reference frame, of an initial orientation of a vertebral plane parallel to at least one end plate of the vertebra in the segment, and
  a calculation of a geometric transformation associated with the vertebra in the segment correlating the initial orientation of the vertebral plane of the vertebrae in the segment with the initial orientation of the location marker associated, the method further comprising:
a step of measuring a displacement of at least one vertebra in the segment, comprising:
  a detection, in the global reference frame, of the current orientation of the location marker associated with said at least one vertebra in the segment, and
  a calculation, in the global reference frame, of the current orientation of the vertebral plane of said at least one vertebra in the segment from the current orientation of the location marker associated and the geometrical transformation associated with said at least one vertebra.

Thus, we can track the displacements of the vertebrae of the vertebral column from the displacements of location markers detected and the orientation of the vertebral planes determined. Such tracking process can be performed in real time, for example during a surgery.

The method can comprise, after the initial step, an identification step comprising:
  a selection of a reference vertebra among the vertebrae in the segment,
  a determination, in the global reference frame, of an initial orientation of at least one reference plane, and
  a calculation of a geometric transformation associated with said at least one reference plane correlating the initial orientation of said at least one reference plane with the initial orientation of the location marker associated with the reference vertebra, the method further comprising, after the measuring step:
  a calculation, in the global reference frame, of the current orientation of said at least one reference plane from the current orientation of the location marker associated with the reference vertebra and the geometric transformation associated with said at least one reference plane,
  a calculation, for each vertebra in the segment, of an angle between the vertebral plane of the vertebra in the segment and said at least one reference plane, and
  a display of the angles calculated.

The method can comprise, after the measurement step, a step in which:
  calculating, for each current orientation of a vertebral plane, an angle between the current orientation of the vertebral plane and the current orientation of another vertebral plane and
  displaying the angles calculated.

The method can further comprise, after the measurement step:
  a projection of each current orientation of a vertebral plane in said at least one reference plane,
  a calculation of the angles between the projections, and
  a display of the angles calculated.

Moreover, the angles between the vertebral planes can be displayed, which constitute a relevant anatomical information relating to the orientation of the end plates. This anatomical information can be used subsequently for correcting the balance of the vertebral column. Advantageously, these values can be displayed in real time, for example during a surgical procedure on the vertebral column.

According to one embodiment, the method comprises an instrument provided with a location marker providing the location system with an orientation vector for a portion of the instrument, and wherein the determination step comprises:
  a first positioning of the portion of the instrument into the vertebral plane of the vertebra in the segment in order to provide a first orientation vector included in said vertebral plane, and
  a second positioning of the portion of the instrument into the vertebral plane of the vertebra in the segment in order to provide a second orientation vector included in said vertebral plane,
  the initial orientation of the vertebral plane of the vertebra in the segment being determined from the first and second vectors provided.

The portion of the instrument can comprise a rod opaque to X-rays, and the orientation vector determines a longitudinal direction of the rod, the method comprising an X-ray emitter and a detector for generating a radiographic X-ray picture of the vertebrae in the segment and the rod, the determination step comprising:
- a display of a radiographic X-ray picture of the vertebra in the segment and the rod,
- a positioning of the X-ray emitter and the detector perpendicularly to the segment so that at least one end plate of the vertebra in the segment is represented by a line in the radiographic X-ray picture, and
- for each positioning of the portion of the instrument, positioning the opaque rod so that it is represented in the radiographic X-ray picture by a line parallel to the line representing said at least one end plate.

The determination step can comprise:
- a first positioning of the portion of the instrument into the vertebral plane of the vertebra in the segment in order to provide a first orientation vector included in the vertebral plane of the vertebra in the segment, and
- a second positioning of the portion of the instrument into a plane perpendicular to said vertebral plane to provide a second orientation vector included in the perpendicular plane,
- the initial orientation of the vertebral plane of the vertebra in the segment being determined from the perpendicular plane and the first orientation vector provided.

In another embodiment, the method can comprise an instrument provided with a location marker providing the location system with an orientation vector, perpendicular to a portion of the instrument, and wherein the determination step comprises:
- a positioning of the portion of the instrument into the vertebral plane of the vertebra in the segment in order to provide an orientation vector perpendicular to the vertebral plane of the vertebra in the segment, and
- the initial orientation of the vertebral plane of the vertebra in the segment is determined from the orientation vector provided.

The portion of the instrument can be a plate.

The plate can be opaque to X-rays, the method comprising an X-ray emitter and a detector for generating a radiographic X-ray picture of the vertebrae in the segment and the plate, and the determination step comprises:
- a display of a radiographic X-ray picture of the vertebra in the segment and the plate,
- a positioning of the X-ray emitter and the detector perpendicularly to the segment so that at least one plate of the vertebra in the segment is represented by a line in the radiographic X-ray picture, and
- a positioning of the plate so that it is represented in the radiographic X-ray picture by a line parallel to the line representing said at least one end plate.

The instrument can comprise at least one sensor, each sensor being capable of detecting a tissue and differentiating between a bone tissue and an intervertebral tissue, and at least one positioning of the portion of the instrument in the vertebral plane is carried out in such a manner that said at least one sensor detects an intervertebral tissue.

The instrument can also be provided with at least one set of at least two sensors, each sensor being capable of detecting a tissue and differentiating between a bone tissue and an intervertebral tissue, the instrument being provided with a location marker providing the location system with an orientation vector perpendicular to a detection plane formed by said at least two sensors, and wherein the determination step comprises:
- a positioning of the instrument so that said at least two sensors detect an intervertebral tissue, and
- the initial orientation of the vertebral plane of the segment is determined from the orientation vector provided.

Moreover, the instrument can comprise a first set of at least two sensors, and a second set of at least two sensors, the orientation vector provided being perpendicular to the detection planes respectively formed by the first and second sets, and the positioning of the instrument comprises a positioning of the sets so that said sets respectively detect two different tissues.

Moreover, the determination step can comprise a display of a grid of reference lines in the radiographic X-ray picture, the reference lines being displayed parallel to each other and to the opaque rod of the instrument. In particular, such a grid allows to facilitate the positioning of the opaque rod into the vertebral plane.

At least one positioning of the portion of the instrument can comprise a positioning of the rod against the detector.

According to still another embodiment, the method comprises an instrument provided with a portion opaque to X-rays, an X-ray emitter and a detector for generating a radiographic X-ray picture of the vertebrae in the segment and the opaque portion, the opaque portion being movably mounted on the detector, and the instrument being further provided with a location marker providing the location system with an orientation vector of the opaque portion and an orientation of a plane of the detector, the determination step comprising:
- a positioning of the X-ray emitter and the detector perpendicularly to the segment so that at least one end plate of the vertebra in the segment is represented by a line in the radiographic X-ray picture, and
- a positioning of the opaque portion of the instrument so that it is represented in the radiographic X-ray picture by at least one line parallel to the line representing said at least one end plate,
- the initial orientation of the vertebral plane being determined from the orientation of the plane of the detector and the orientation vector of the opaque portion.

Moreover, the determination step can comprise a picture processing operation for calculating an orientation of the line representing said at least one end plate, an orientation of the line representing the rod, and an angle between said orientations of the lines.

The method may further comprise a step of displaying the angle between said orientations of the lines.

The initial orientation of the vertebral plane of the vertebra in the segment can be corrected from the angle between said orientations of the lines.

In another embodiment, the portion of the instrument is opaque to X-rays, the method comprising an X-ray emitter and a detector for generating a radiographic X-ray picture of the vertebrae in the segment and the opaque portion, the determination step comprising:
- a display of a radiographic X-ray picture of the vertebra in the segment and the opaque portion,
- a positioning of the X-ray emitter of the detector perpendicularly to the segment so that at least one end plate of the vertebra in the segment is represented by a line in the radiographic X-ray picture,
- at least one positioning of the portion of the instrument comprising a positioning of the opaque portion so that it is represented by a line in the radiographic X-ray picture, and
- a picture processing operation for calculating an orientation of the line representing said at least one end plate, an orientation of the line representing the opaque portion, and an angle between said orientations of the lines, the initial orientation of the vertebral plane being corrected from the angle calculated.

BRIEF DESCRIPTION OF THE DRAWINGS

Other advantages and features will become more apparent from the following description of particular embodiments of the invention given as non-restrictive examples only and represented in the accompanying drawings, wherein.

DETAILED DESCRIPTION

Figure 1:
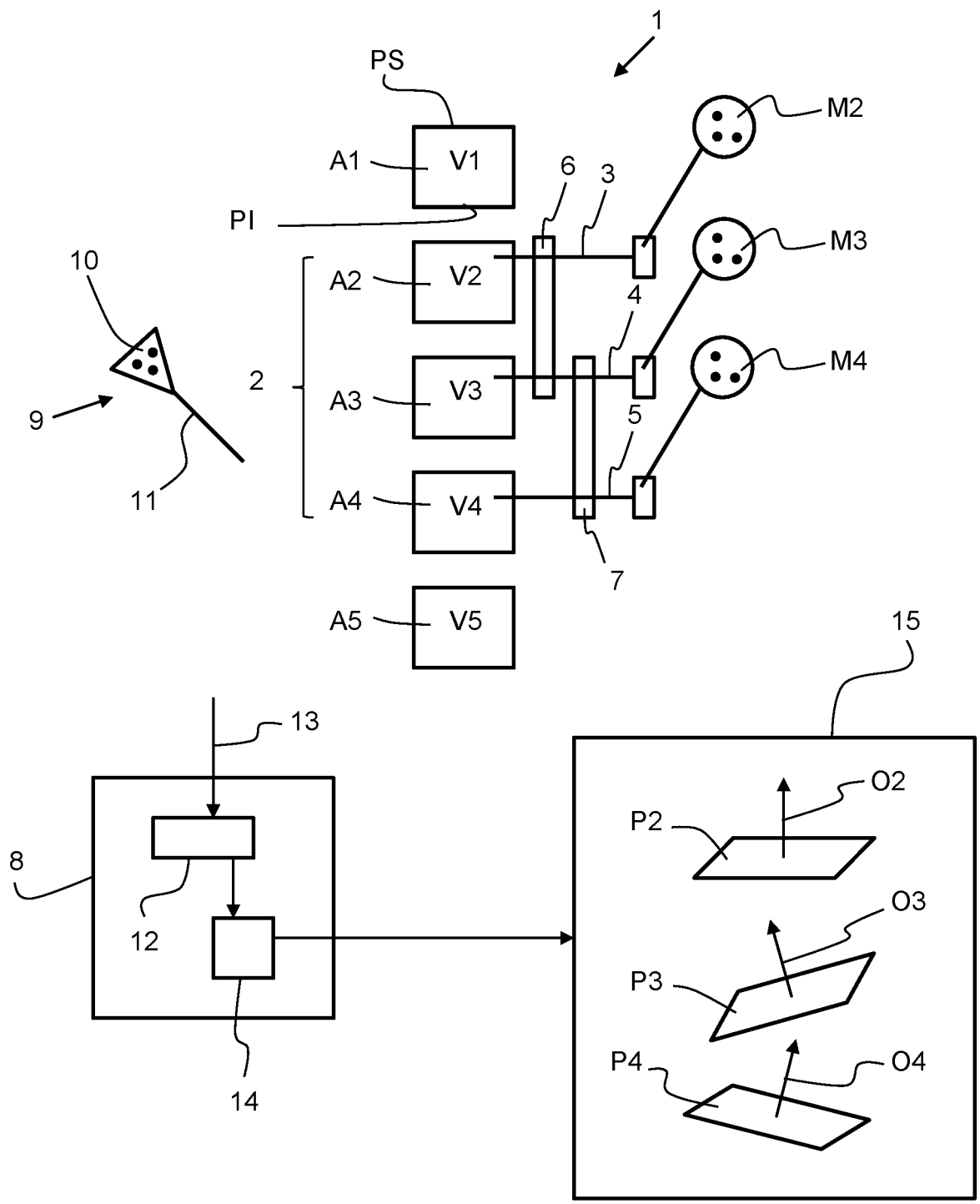
FIGS. 1 and 2 schematically illustrate the main steps of a method for measuring the displacements of a vertebral column according to the invention, FIGS. 3 and 4 schematically illustrate variants of a first embodiment of the measurement method, FIG. 5 schematically illustrates an embodiment of a means for guiding the positioning of an instrument, FIGS. 6 to 8 schematically illustrate variants of a second embodiment of the measurement method, and FIG. 9 schematically illustrates exemplary further steps (to be taken in combination with the above-noted main steps) of a method for measuring the displacements of a vertebral column according to the invention.
Figure 2:
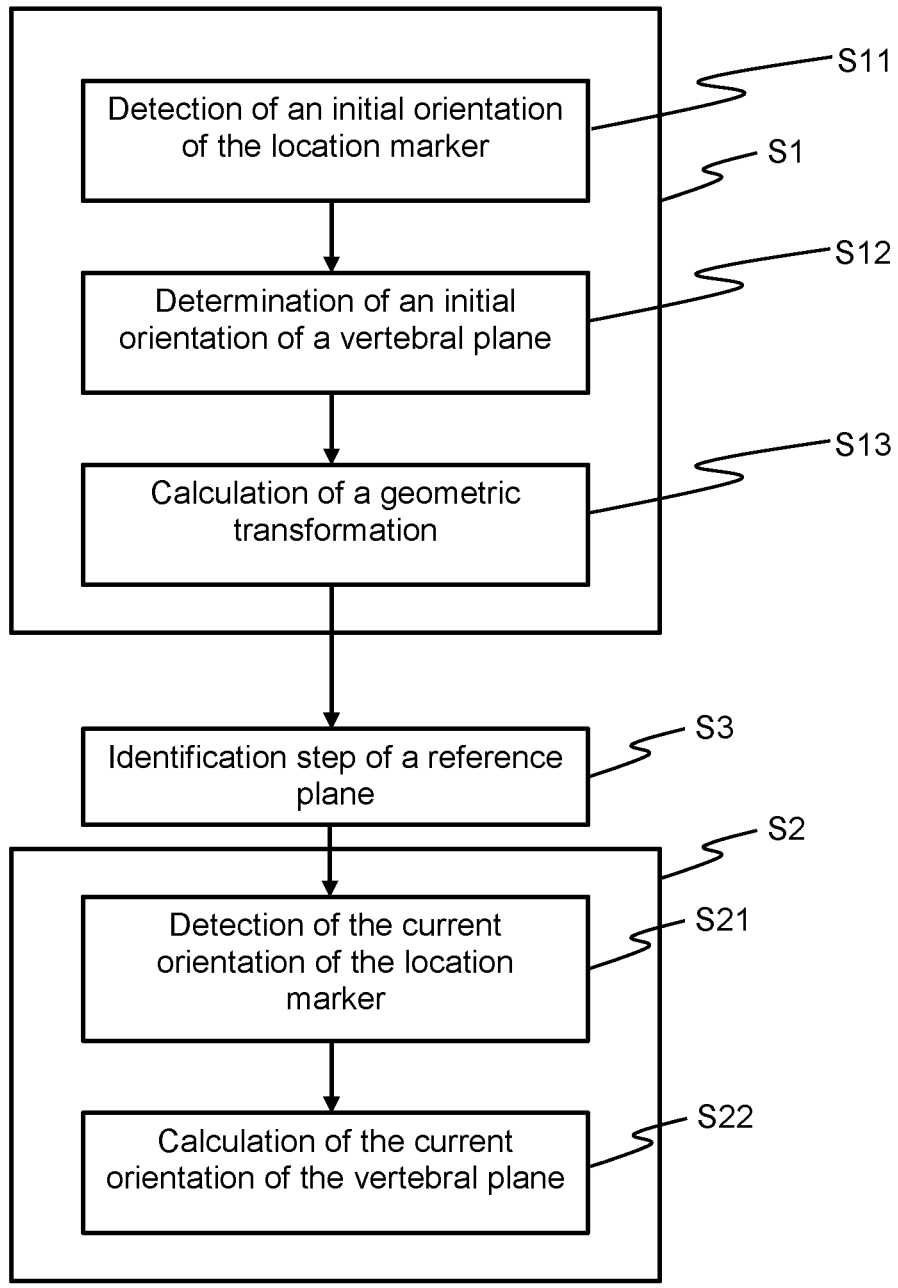

FIGS. 1 and 2 show the main steps of a method for measuring the displacements of a vertebral column 1. The vertebral column 1 comprises several vertebrae V1 to V5. In particular, the method consists in tracking the displacements of the vertebrae comprising at least one vertebral end plate. A segment 2 of the vertebral column 1 is then selected, which comprises at least one vertebra V2 to V4, each vertebra in the segment comprising a body A1 to A5 delimited by an upper end plate PS and a lower end plate PI. In order to track the displacement of the vertebrae in the segment, a vertebral plane P2 to P4 is identified for each vertebra in the segment, i.e. a plane associated with a vertebra in the segment. The vertebral plane of a vertebra in the segment 2 is a plane parallel to at least one end plate of the vertebra in the segment 2, for example the upper end plate PS. The vertebral end plate PS, PI of a vertebra in the segment 2 corresponds to a side of the body A2 to A4 of the vertebra. As for the vertebral plane associated with the vertebra in the segment, it corresponds to a virtual plane used for measuring the displacements of the vertebra in the segment. FIG. 1 schematically represents a section of the vertebral column 1 comprising five consecutive vertebrae V1 to V5. The segment 2 comprises three consecutive vertebrae V2 to V4 corresponding to the vertebrae whose displacements are to be tracked, especially during a surgical operation. The vertebra segment 2 can comprise a single vertebra V2 or more vertebrae V2 to V4, consecutive or not, such as in the sacrum. For example, the segment 2 can comprise a single lumbar vertebra, located in the lower part of the vertebral column. Alternatively, the segment 2 comprises a cervical vertebra, located in the upper part of the vertebral column, and a thoracic vertebra located in the intermediate part of the vertebral column. In another example, the segment 2 can comprise five consecutive thoracic vertebrae.

Furthermore, each vertebra V2 to V4 of the segment 2 comprises an associated location marker M2 to M4 attached to the vertebra V2 to V4. In other words, each marker M2 to M4 is mechanically connected to the vertebra V2 to V4 associated therewith. When a vertebra in the segment 2 is displaced, the location marker associated is also displaced. The markers M2 to M4 can be connected directly to the vertebrae in the segment 2, for example on the body A2 to A4 of the vertebrae. Preferably, screws 3 to 5 are attached to the vertebrae in the segment 2, and connecting members 6, can connect the screws 3 to 5 with one another. The screws 3 to 5 and the connecting members 6, 7 are used to modify the curvature of the vertebral column 1, and therefore the position and orientation of the vertebrae V2 to V4 of the segment 2. The markers M2 to M4 can also be attached to the screws 3 to 5, as illustrated in FIG. 1. They can also be attached to the connecting members 6, 7, if these are rigidly attached to the screws 3 to 5. Each vertebra in the segment for which it is desired to determine a vertebral plane P2 to P4, is equipped with an associated location marker M2 to M4, these vertebrae are also called instrumented vertebrae.

Generally, the method comprises an initial step S1, in which, for each vertebra in the segment, an initial orientation of the vertebral plane of the vertebra relative to the location marker associated is determined, then a step S2 is determined for measuring displacements of the vertebrae in the segment, in particular displacements of at least one vertebra in the segment, by tracking the displacement of the location markers. 'Orientation of a plane' means a vector normal to the plane. Likewise, 'orientation of a location marker' means a rotation transformation associated with the marker. In order to measure the displacement of the vertebral column, a location system 8 is used to determine the spatial position and orientation of an object. Moreover, an instrument 9 comprising at least one location marker 10 is used to provide the location system 8 with an orientation of a portion of the instrument 11. More particularly, each of the location markers M2 to M4 and 10 comprises at least three position sensors. The location system 8 can detect the position and orientation provided by each location marker M2 to M4 associated with the vertebrae in the segment and by the location marker 10 of the instrument 9. The location system 8 comprises a localizer 12 which can be for example an optical or magnetic localizer, and which receives, through a wired or unwired connection 13, the information provided by the location markers M2 and M4 and by the location marker 10 of the instrument 9. The localizer 12 can track in real time the position and orientation of each location marker M2 to M4 associated with the vertebrae and the position and orientation of the location marker 10 of the instrument 9. In other words, each location marker M1 to M3 associated with a vertebra in the segment 2 and that of the instrument 9 provide at least one orientation of the location marker in a global reference frame of the location system 8. That is to say, the location system 8 is used as a global reference frame for all measurements of the orientations of the location markers M2 to M3, 10. For example, the location system 8 can be an optical camera and the location markers M2 to M4 and 10 are reflective pads or marks having a specific color, or shape, adapted to be located by the camera. The location markers M2 to M4 and 10 can also comprise light emitting diodes localizable by the camera.

In general, the initial step S1 comprises for each vertebra V2 to V4 of the segment 2:
  a detection S11, in the global reference frame, of an initial orientation of the location marker M2 to M4 associated with the vertebra in the segment 2,
  a determination S12, in the global reference frame, of an initial orientation of a vertebral plane P2 to P4 parallel to at least one end plate of the vertebra in the segment 2, and a calculation S13 of a geometric transformation associated with the vertebra in the segment correlating the initial orientation of the vertebral plane of the vertebra in the segment with the initial orientation of the location marker associated.

The geometric transformation associated with a vertebra is used to link the orientation of the vertebral plane of the vertebra with that of the location marker associated. The geometric transformation comprises rotation and translation transformations. In other words, the geometrical transformation is used to calculate the relative orientation of the vertebral plane relative to that of the location marker associated. When the vertebra is displaced, through a rotation and/or a translation, the location marker associated performs the same displacement. The new orientation of a location marker M2 to M4, due to the displacement of the vertebra associated therewith, is then detected S21 and the new orientation O2 to O4 of the vertebral plane of the vertebra is calculated S22 from the geometric transformation calculated and the new orientation of the location marker. The new orientations of the location markers M2 and M4 and the vertebral planes P2 to P4 are also called current orientations. The calculation step S22 of the measurement step is used to track the orientations O2 to O4 of the vertebral planes of the instrumented vertebrae over time.

In addition, the method can comprise, after the initial step S1, an identification step S3 in which one or more reference planes are identified, and the respective angles between the current orientations of the vertebral planes and the current orientation of at least one reference plane identified are calculated. The current orientations of the vertebral planes can also be projected in each reference plane. Then, the angles between the projections obtained are determined, in each reference plane. In particular, the angle of a vertebral plane can be determined relative to another vertebral plane, or the angles between each vertebral plane and a vertebral reference plane, for example the vertebral plane associated with the sacrum, can be determined. 'Angle between two planes' means the angle between two vectors normal to the planes, respectively. The angles between the vertebral planes also correspond to the angles between the vertebral end plates of the vertebrae in the segment. The calculation of the angles between vertebral planes especially gives the true angles between the end plates of the vertebrae. Moreover, the angles between the projections of the current orientations obtained in each reference plane having an anatomical interest can be displayed in real time.

The identification step S3 can comprise:
a selection of a reference vertebra among the vertebrae in the segment,
a determination, in the global reference frame, of an initial orientation of at least one reference plane, and
a calculation of a geometric transformation associated with said at least one reference plane correlating the initial orientation of said at least one reference plane with the initial orientation of the location marker associated with the reference vertebra, the method further comprising, after the measurement step:
a calculation, in the global reference frame, of the current orientation of said at least one reference plane from the current orientation of the location marker associated with the reference vertebra and geometric transformation associated with said at least one reference plane,
a calculation, for each vertebra in the segment, of an angle between the vertebral plane of the vertebra in the segment and said at least one reference plane, and
a display of the angles calculated.

Figure 3:
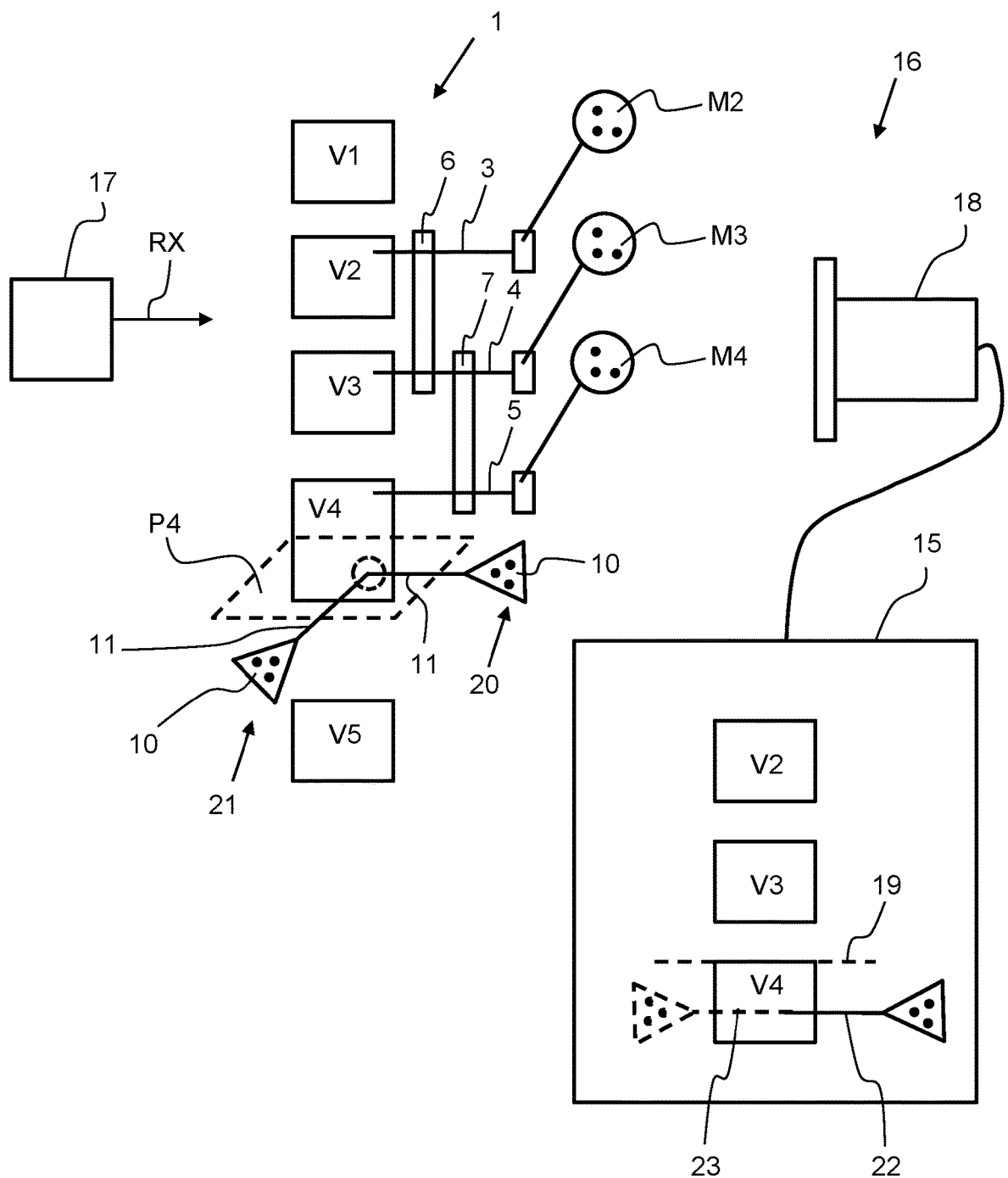

More particularly, the location system 8 can comprise a processing unit 14, e.g. a microprocessor, for calculating an angle between a vertebral plane and each reference plane, as well as the angles between the vertebral planes, or the angles between the projections of the current orientations of the vertebral planes. The location system 8 can be connected with a display panel 15 for displaying the orientations O2 to O4 of the vertebral planes P2 to P4. In order to determine the initial orientation of the vertebral planes, several embodiments can be carried out. In a first embodiment, shown in FIGS. 3 and 4, the instrument 9 is used, which is provided with the location marker 10 providing the location system 8 with an orientation vector for the portion 11 of the instrument. For example, the instrument 9 can be a navigation pointer, and the portion of the instrument is a rod. The navigation pointer 9 allows to locate specific anatomical points of the column, and in particular to provide the location system 8 with an orientation vector for the rod 11, the orientation of the rod is defined during the manufacture of the instrument, or by calibration relative to the position and orientation of the position sensors of the location marker 10. In order to determine the orientation of a vertebral plane of a vertebra in the segment, the rod 11 is placed in a first position 20 in the plane P4 of the vertebra in the segment. Then, an acquisition of the orientation vector for the rod 11, triggered for example from the instrument 9, is carried out, which provides the location system 8 with a first orientation included in the vertebral plane P4. Then, the rod 11 is moved into a second position 21 also in the vertebral plane P4, and a second acquisition is triggered so as to provide a second orientation vector in the vertebral plane P4. Then, the location system 8, especially the processing unit 14, determines the initial orientation of the vertebral plane from both orientation vectors provided by the navigation pointer 9. FIG. 3 shows an example of the first embodiment. In this example, the rod 11 is placed in abutment against the body of an instrumented vertebra V4, so that the rod 11 is located in the vertebral plane. The first positioning 20 can be visually carried out by placing the rod 11 in parallel with one of the end plates PI, PS of the vertebra V4. The positioning of the rod 11 can also be improved with the help of below-described guiding means. Then, the rod 11 is pivoted into the second position 21 in the vertebral plane P4, for example while maintaining a contact of the end of the rod in abutment against the vertebra V4, and a second acquisition is triggered so as to provide the location system 8 with a second orientation vector in the vertebral plane P4. When the localizer 12 has received the two orientation vectors, it sends them to the processing unit 14, which determines the initial orientation of the vertebral plane of the instrumented vertebra V4 from the two orientation vectors provided. In particular, the processing unit 14 determines the vector normal to the two vectors provided, corresponding to the initial orientation of the vertebral plane P4. For example, the rod 11 is brought closer to the column 1 by an operator, and when the end of the rod 11 comes into contact with the instrumented vertebra, the location marker 10 of the navigation pointer 9 transmits an information data about the orientation of the rod 11 to the localizer 12. In addition, the end of the rod 11 can be in direct contact with the bone of the vertebra, or a screw 3 to 5, or a connecting element 6, 7, or the location marker associated with the instrumented vertebra V4. The contact can also be an indirect percutaneous contact with the skin at a point where the vertebra is located. The acquisition of the orientation of the rod 11 of the navigation pointer 9 can also be carried out without contact, so that the rod 11 is parallel to at least one vertebral end plate.

In addition, the navigation pointer 9 can be used to determine the orientation of the sagittal, frontal and axial reference planes during the identification step S3.

Alternatively, the determination of an orientation of a vertebral plane can comprise a determination of the vertebral plane, then a determination of a vector normal to the vertebral plane determined. The normal vector corresponds to the orientation of the vertebral plane. The determination of a vertebral plane can comprise an acquisition of the position of a point in the vertebral plane and an acquisition of the orientation of a vector in the vertebral plane, or the acquisition of the position of three points in the vertebral plane, or, as described above, the acquisition of the orientation of two vectors in the vertebral plane.

In order to improve the positioning of the rod 11 in the vertebral plane, an X-ray imager 16 can be used, which comprises an x-ray (designated RX) emitter 17 and a detector 18 for the X-rays emitted. In this case, the rod 11 of the navigation pointer 9 is a rod 11 opaque to X-rays. In addition, the orientation vector provided by the location marker 10 corresponds to a longitudinal direction of the rod 11. The emitter 17 and the receiver 18 are used to generate a radiographic X-ray picture of the vertebrae in the segment and the opaque rod 11. The determination step comprises for each vertebra in the segment 2:

a display of a radiographic X-ray picture of the vertebra in the segment V2 to V4, and the opaque rod 11 of the display panel 15, a positioning of the X-ray emitter 15 and the detector 16 perpendicularly to the segment 2 so that at least one end plate PI, PS of the vertebra in the segment is represented by a line 19 in the radiographic X-ray picture, and for each positioning of the portion of the instrument, the opaque rod 11 is positioned so that it is represented by a line in the radiographic X-ray picture parallel to the line 19 representing said at least one end plate.

The line 19 representing at least one end plate, also designated the guiding line, is used as a guiding means for facilitating the positioning of the rod of the instrument in the vertebral plane.

A line 19 appears in the picture when the emitter 17 and detector 18 are located in a particular position, so-called perpendicular position relative to the vertebrae segment 2. In this perpendicular position, at least one end plate of the vertebra in the picture is represented as a line 19. This line 19 is virtual. In particular, are displayed two-dimensional pictures of the bodies of the instrumented vertebrae, and at least one end plate PS, PI of an instrumented vertebra V2 to V4 in the form of a generally linear curve corresponding to the guiding line 19. Indeed, when the emitter and the detector are not oriented perpendicularly to the segment, the end plate of the instrumented vertebra appears in the picture as a surface and not as a generally linear curve, which does not allow to locate in the picture the end plate of a vertebra in the form of a line.

During the steps of positioning the portion of the instrument, the rod 11 of the navigation pointer 12 is placed on a vertebra V4, in the first position 20 and the position of the rod 11 in the picture is displayed on the display panel 15. The operator adjusts the position of the rod 11 so that on the display panel 15 the rod of the navigation pointer 9 appears as a line 22 parallel to the guiding line 19. In the first position 20, the first orientation of the rod 11 is detected.

Then, the operator moves the rod 11 of the navigation pointer 12 into the second position 21, so that on the display panel 15 the rod of the navigation pointer appears as a line 23, shown here as a dotted line parallel to the guiding line 19. Thus, the imager 16 allowing to locate the guiding line 19 in the picture, allows to guide the different positionings of the rod 11 of the navigation pointer 9 so that the rod is located in the vertebral plane P4 of the instrumented vertebra V4. In particular, the display of the pictures of the segment 2 of the vertebral column is carried out during the determination step S12 of the initial orientations of the vertebral planes. The imager 16, comprising the emitter 15 and detector 16, allows to control the position of the instrument 9 with respect to the end plates. Thus, the operator can correct the positioning of the instrument relative to the guiding line 19.

Figure 4:
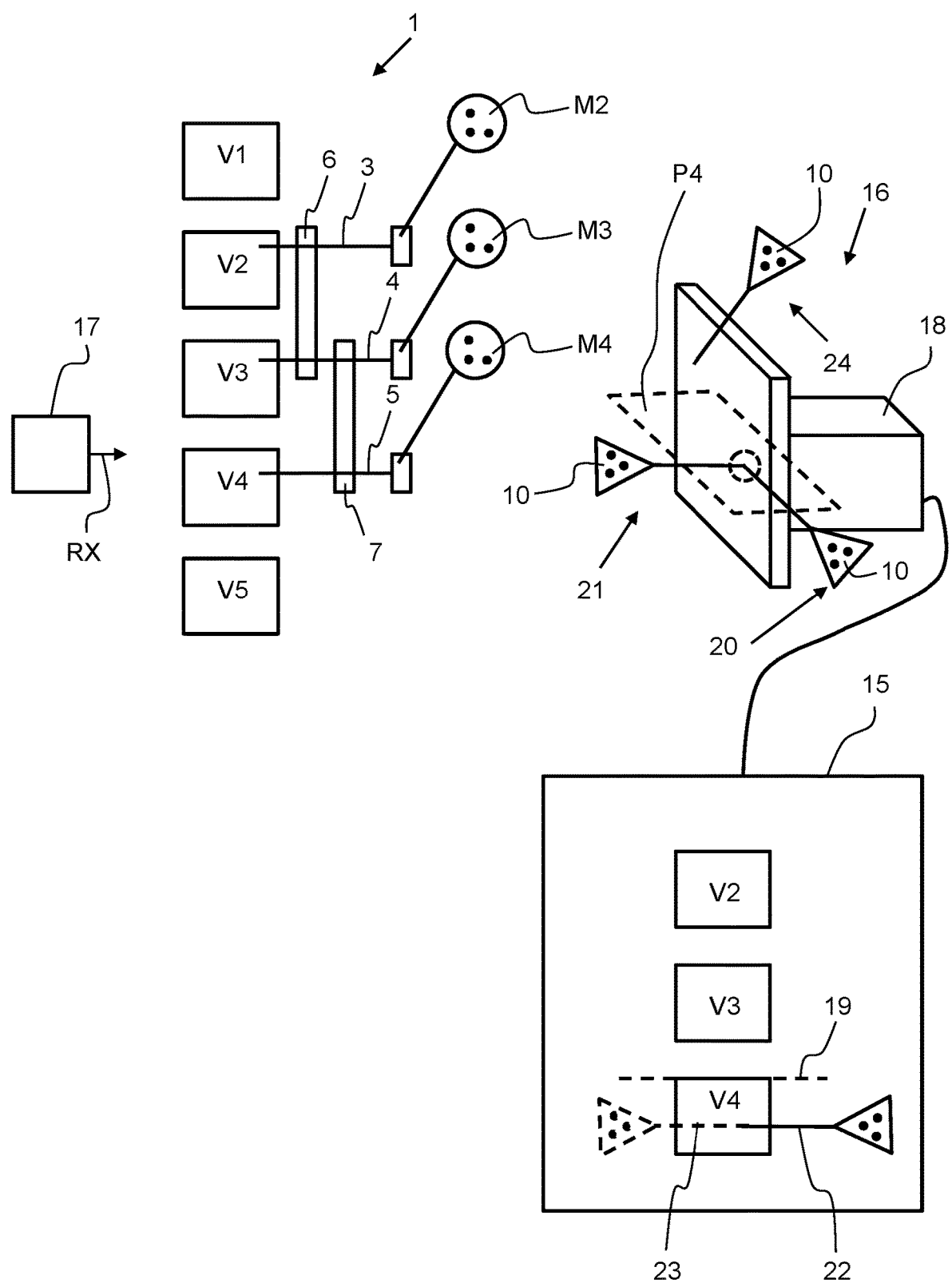

FIG. 4 shows two other variants of the first embodiment. In a first variant, the first positioning 20 of the opaque rod 11 of the navigation pointer 12 comprises a positioning of the opaque rod against the detector 16. Thus, keeping the rod 11 in the vertebral plane is facilitated during the acquisition of the orientation of the rod 11. Indeed, the operator manipulating the navigation pointer can use the detector 18 as a support. Then, the operator rotates the rod 11, by using the detector as a support, i.e. by keeping the end of the rod 11 in contact with the detector 18, and moves the rod 21 into the second position, i.e. into the vertebral plane P4, in order to provide the location system 8 with the second orientation. In this first variant, it is not necessary to position the navigation pointer onto the body of an instrumented vertebra.

In the second variant, the determination step comprises:

a first positioning 20 of a portion 11 of the instrument 9 in the vertebral plane of the vertebra in the segment in order to provide a first orientation vector in said vertebral plane, and a second positioning 24 of the portion 11 of the instrument 9 in a plane perpendicular to said vertebral plane in order to provide a second orientation vector in the perpendicular plane, the initial orientation of the vertebral plane of the vertebra in the segment being determined from the perpendicular plane and the first orientation vector provided.

According to this second variant, during the second positioning, the rod 11 is placed against the detector 24 in a second position distinct from the first position, in particular in a position which is not in alignment with the first orientation of the rod 11. In this case, the two orientations provided are in a plane perpendicular to the vertebral plane because the detector is first located in a plane perpendicular to the vertebral plane. In particular, the initial orientation of the vertebral plane corresponds to the vector normal to the plane which is perpendicular to the plane formed by the two vectors provided and comprises the first orientation vector provided.

Figure 5:
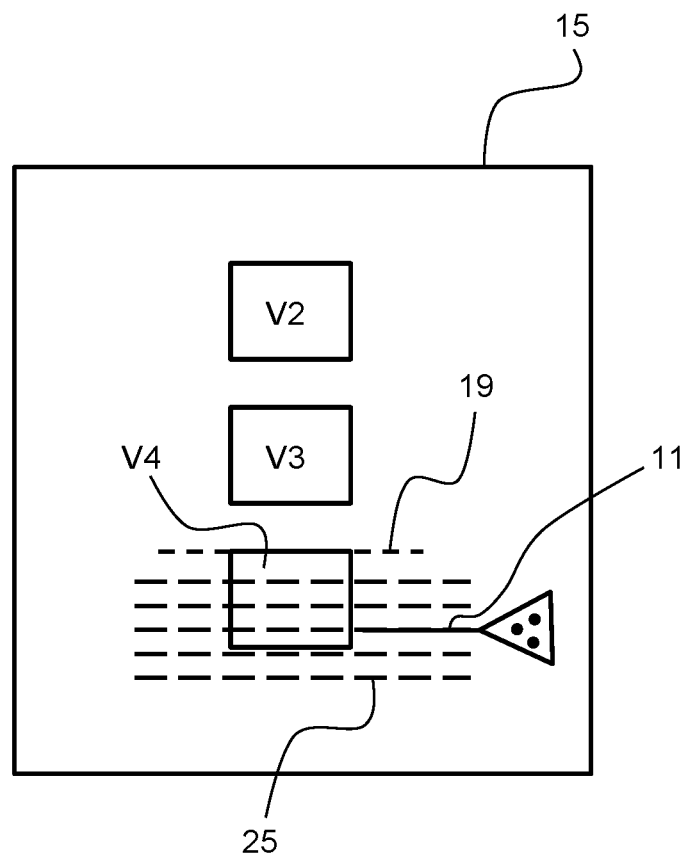

FIG. 5 shows another means for guiding the positioning of the opaque rod 11 of the navigation pointer 9. The means comprises a grid 25 of reference lines parallel to one another. The grid 25 is calculated by the processing unit 14 and then displayed in the radiographic X-ray picture so that the reference lines are parallel to the opaque rod 11. When the operator changes the direction of the opaque rod 11, the processing unit 14 also changes the direction of the reference lines on the display panel 15.

An alternative means can be used for guiding the positioning of the instrument 9. This alternative means is at least one detection sensor for a type of tissue. Each detection sensor is included in the instrument 9, and is configured so as to detect and differentiate between a bone tissue and a vertebral tissue. In particular, the bone tissue corresponds to that of the body of a vertebra and the intervertebral tissue corresponds to the specific tissue between two consecutive vertebrae of the vertebral column. During the determination step S12, the portion 11 of the instrument 9 is positioned into a vertebral plane so that the sensor of the instrument 9 detects an intervertebral tissue, more particularly the intervertebral tissue against the end plate of the instrumented vertebra. The detection sensors allow to guide the operator in order to improve the accuracy of the positioning of the instrument 9. Indeed, as long as the detection sensor detects an intervertebral tissue, the instrument 9, and in particular the portion 11 of the instrument, is generally located in the vertebral plane. Alternatively, the positioning of the instrument can also be specified by equipping the instrument with at least two detection sensors. In this variant, when a first sensor detects an intervertebral tissue and a second sensor detects a bone tissue, the portion 11 of the instrument is located in the vertebral plane with a greater accuracy. Indeed, if the portion of the instrument is outside the vertebral plane, i.e. tilted relative to the vertebral end plate, both detection sensors then detect bone tissue.

Figure 6:
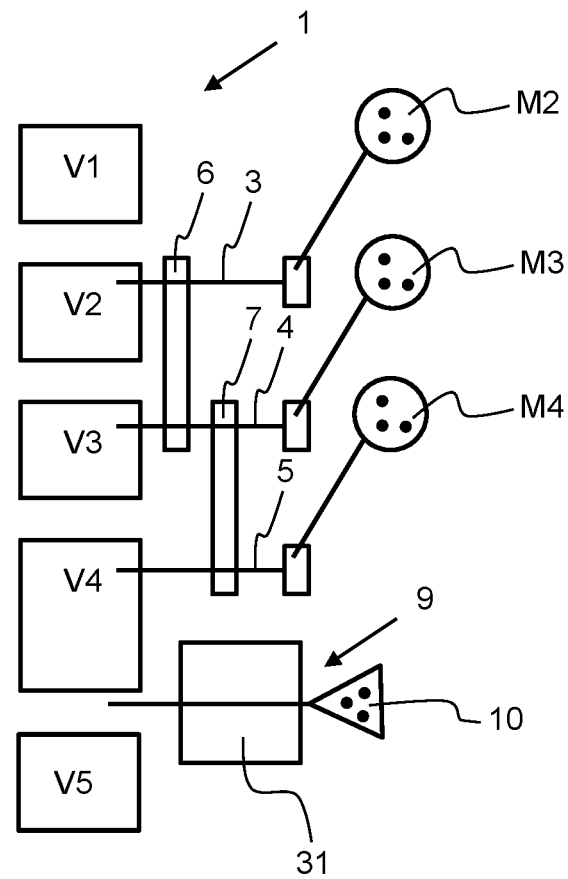
Figure 7:
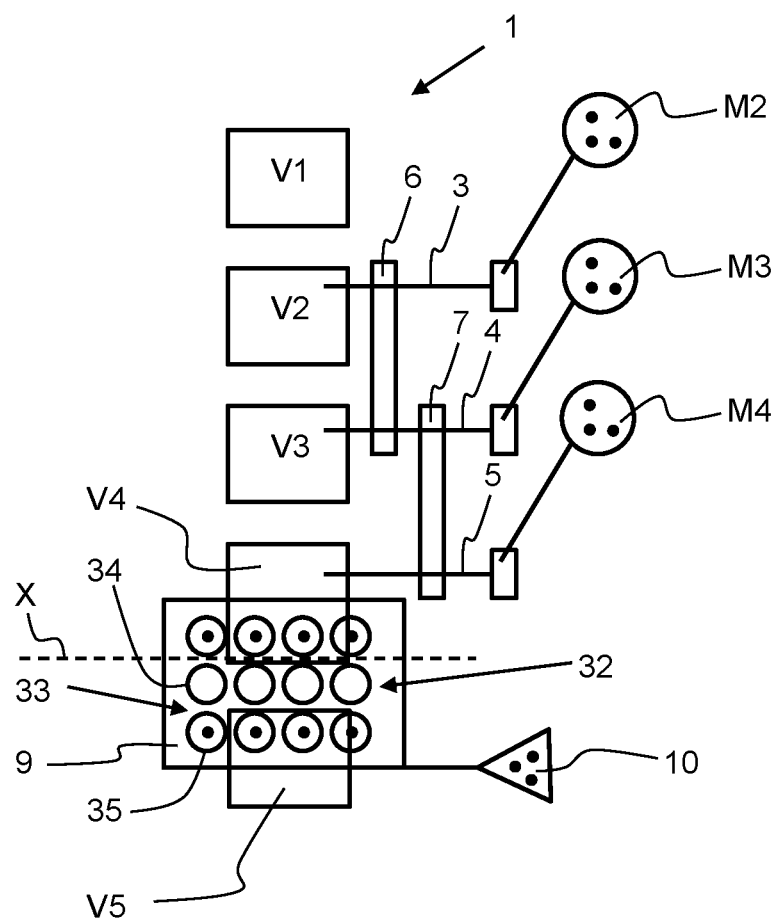

FIGS. 6 and 7 show two examples of a second embodiment of the method. In this second embodiment, the location marker 10 of the instrument 9 provides the location system 8 with an orientation vector, perpendicular to a portion of the instrument. Furthermore, the determination step S12 comprises:

a positioning of the portion 11 of the instrument 9 into the vertebral plane of the vertebra in the segment in order to provide an orientation vector perpendicular to the vertebral plane of the vertebra in the segment, and the initial orientation of the vertebral plane of the vertebra in the segment is determined from the orientation vector provided.

Thus, the initial orientation of the vertebral plane is directly obtained because it corresponds to the orientation vector provided by the location marker 10 of the instrument 9. A single positioning of the instrument can then be carried out in order to obtain the orientation of a vertebral plane, which simplifies the method.

FIG. 6 shows a first example of the second embodiment, wherein the instrument 9 comprises a plate 31. The location marker 10 of the instrument 9 provides an orientation vector perpendicular to the plane of the plate 31. The determination step S12 comprises a positioning of the plate 30 into the vertebral plane of the vertebra in the segment. Moreover, the plate 31 allows to guide the operator in order to visually position the plate 31 into the vertebral plane of the instrumented vertebra. FIG. 6 shows, for purposes of simplification, the plate 31 in the plane of the sheet, i.e. in a plane perpendicular to a vertebral plane of a vertebra in the segment. When positioning the plate 31, the operator rotates the instrument 9 in order to move the plate 31 into a plane parallel to at least one end plate of a vertebra V2 to V4 of the segment 2, i.e. into the vertebral plane of the vertebra V2 to V4. For example, the plate 31 can be opaque to X-rays and the imager 16 can be used to guide the positioning of the plate into the vertebral plane. More particularly, the positioning of the portion of the instrument comprises a positioning of the plate 31 so that it is represented by a line in a radiographic X-ray picture parallel to the line 19 representing said at least one end plate. The above-described guiding means can then be used to improve the positioning of the plate 31 into the vertebral plane.

FIG. 7 shows the second example of the second embodiment of the method, wherein the instrument includes a first set of at least two detection sensors 34. Each sensor is capable of detecting a tissue and differentiating between a bone tissue and an intervertebral tissue. In particular, each detection sensor detects a type of tissue down to a determined depth specific to the characteristics of the sensor. Preferably, the determined depth corresponds to a maximum thickness of the vertebral column. The instrument 9 can be an ultrasonic probe, or an electrical-impedance probe or a Terahertz sensor. The positioning of the portion 11 of the instrument comprises a positioning of a first set of at least two sensors so that the set detects an intervertebral tissue. The instrument 9 is positioned between the vertebra V4 of the segment 2 and an adjacent vertebra V5 so that the instrument 9 detects the intervertebral tissue between said adjacent vertebrae. FIG. 7 shows this detection by the sensors 34 represented as open circles. Furthermore, the instrument 9 comprises a location marker 10 providing the locating system 8 with an orientation vector perpendicular to a detection plane formed by said at least two sensors. The detection plane corresponds to the plane in which the detection signals of the sensors propagate in order to detect the types of tissue. When the set 32 of sensors 34 detects an intervertebral tissue, the detection plane is parallel to at least one end plate of an instrumented vertebra. In FIG. 7, the detection plane is perpendicular to the plane of the sheet, it is represented by the dotted line X. In order to further improve the accuracy of the positioning of the instrument 9, this instrument can comprise a second set 33 of at least two sensors 35, and the location marker 10 provides an orientation vector perpendicular to the detection planes respectively formed by the first and second sets. More particularly, the detection planes of the sets of sensors are parallel to one another. Thus, the positioning of the instrument 9, for providing an orientation vector perpendicular to the vertebral plane of an instrumented vertebra, is carried out so that the set 32, 33 of sensors respectively detect two different tissues. In FIG. 7, the first set 32 of sensors 34 detects an intervertebral tissue, the detection of the intervertebral tissue is illustrated by the sensors 34 represented as open circles, and the second set 33 of sensors 35 detects a bone tissue, the detection of the bone tissue is illustrated by the sensors 35 represented as circles having points at their centers. When at least the first sensor 32 detects an intervertebral tissue and at least the second set of sensors 33 detects a bone tissue, the probe is placed correctly, i.e. the detection planes formed by the sensors 34, 35 are parallel to at least one end plate of the vertebra V5. Then, the orientation vector provided by the instrument corresponds to the initial orientation of the vertebral plane. Furthermore, as long as no set of sensors detects the intervertebral tissue, the instrument is not correctly positioned and the plane separating the sets of sensors is not parallel to at least one vertebral end plate of the vertebra V5 in the segment 2.

Figure 8:
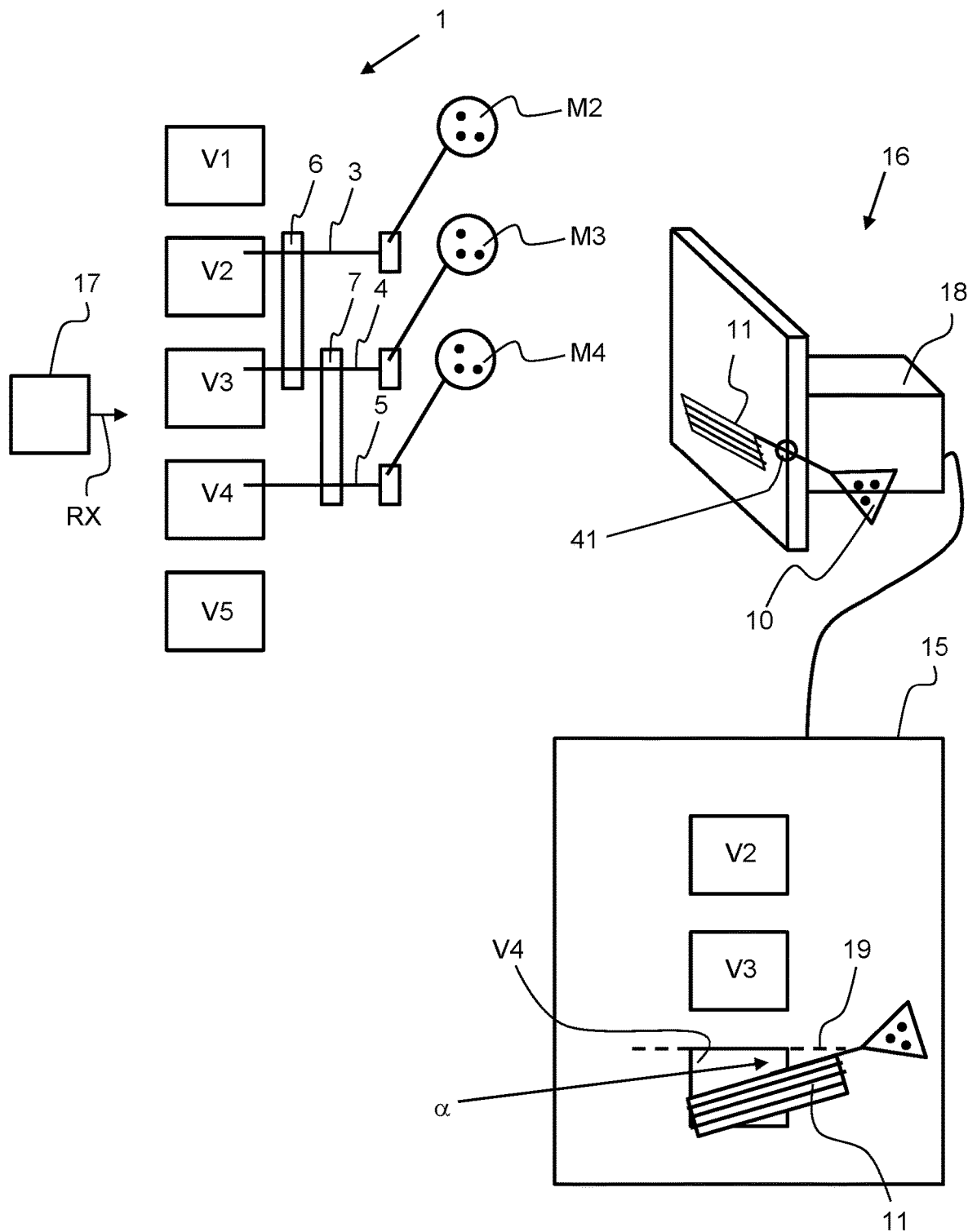
Figure 9:
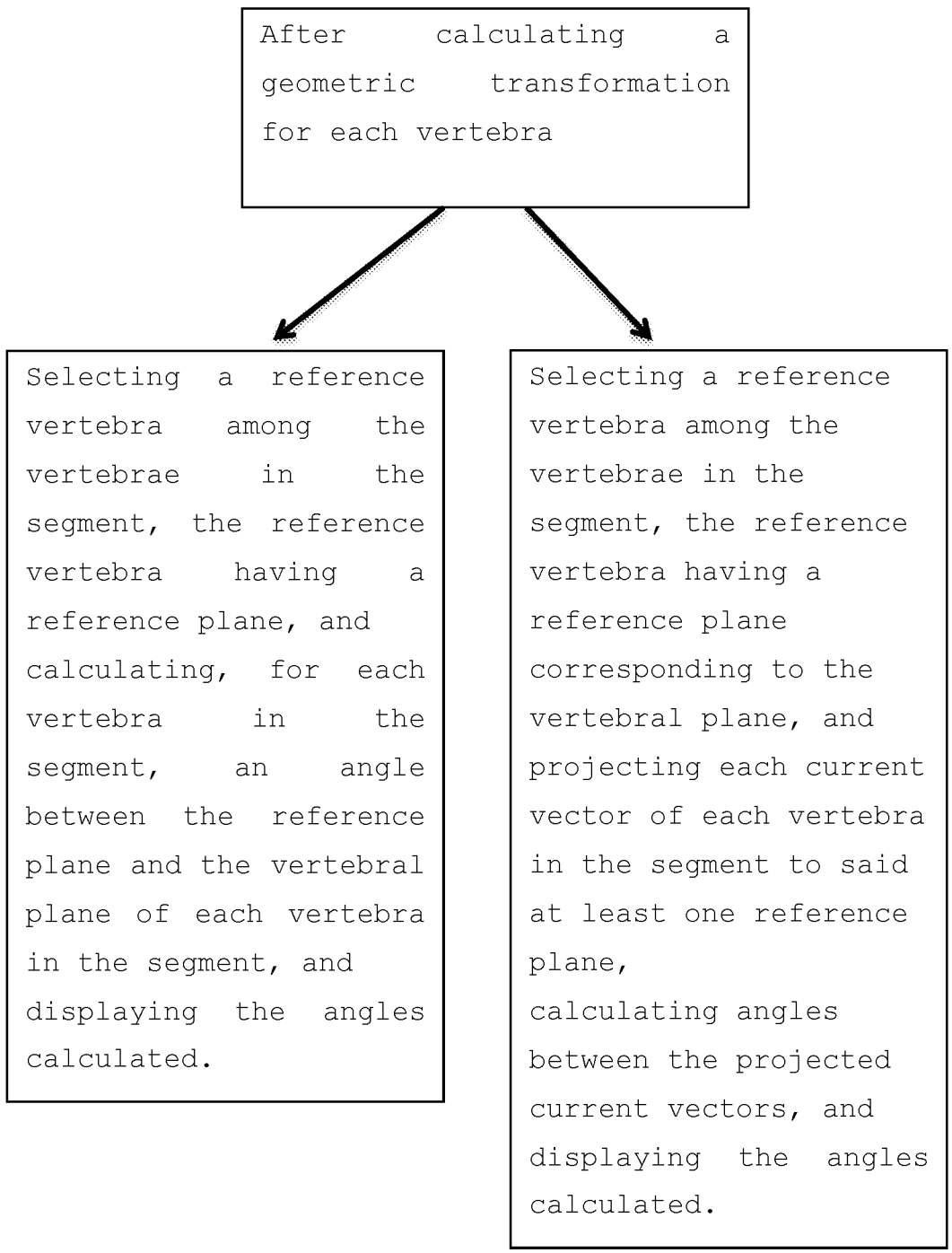

FIG. 8 shows still another embodiment of the determination step S12 for the initial orientations of the vertebral planes P2 to P4. In this other embodiment, the instrument 9 is provided with a portion 11 opaque to X-rays, and an X-ray imager 16 is used to generate a radiographic X-ray picture of the vertebrae in the segment and the opaque portion. Furthermore, the opaque portion 11 is movably mounted on the detector 18. The instrument 9 is also provided with a location marker providing the location system 8 with an orientation vector of the opaque portion and an orientation of a plane of the detector. Generally, the instrument can be any system calibrated for providing the location system 8 with an orientation vector of the opaque portion and an orientation of a plane of the detector. For example, the opaque portion 11 is a rod attached to a point 41 of the detector 18 and able to pivot about this point 41. Alternatively, the opaque portion 11 is a plate, represented by hatching in FIG. 8, which can slide in a sliding rail mounted so as to move in translation on the detector 18.

The determination step S12 comprises:
a positioning of the X-ray emitter and detector perpendicularly to the segment so that at least one end plate of the vertebra in the segment is represented by a line in the radiographic X-ray picture, and
a positioning of the opaque portion 11 of the instrument so that it is represented in the radiographic X-ray picture by at least one line parallel to the line representing said at least one end plate,
the initial orientation of the vertebral plane being determined from the orientation of the plane of the detector and the orientation vector of the opaque portion.

As the opaque portion 11 is movable, the operator can adjust its positioning relative to the line 19 representing said at least one end plate. When the line representing the opaque portion is parallel to the line 19 representing said at least one end plate, the detector plane is perpendicular to the vertebral plane, and the orientation vector of the opaque portion is located in the vertebral plane of the instrumented vertebra. The initial orientation of the vertebral plane corresponds to the vector perpendicular to the orientation vector of the opaque portion and the orientation of the plane of the detector.

Moreover, the determination step S12 can comprise a picture processing step, carried out by the processing unit 14 in order to calculate, from the radiographic X-ray picture of the vertebrae in the segment, the orientations of the lines representing said at least one end plate of the vertebrae V2 to V4 in the segment 2. The picture processing step is also carried out in order to calculate the orientations of the line representing the opaque portion 11 of the instrument 9. Then, the angle α between said orientations of the lines are calculated for each vertebra in the segment. This angle α corresponds to a parallelism defect between the positioning of the opaque portion of the instrument and the line 19 representing the end plate of the vertebra in the segment. When the angle α is zero, the opaque portion is parallel to the guiding line 19. The value of the angle can then be displayed on the display panel 15 in order to indicate the parallelism defect and to guide the operator so that she/he can position the instrument correctly. The value of the angle α can also be used to correct the initial orientation of the vertebral plane of the vertebra in the segment. In this case, the processing unit determines the initial orientation of the vertebral plane directly from the angle calculated.

The above-defined method allows to evaluate the displacements of a vertebral column for correcting the balance of the column. Furthermore, such an evaluation can be carried out in real time.

It may be noted that various modifications can be made to the embodiments of the invention, described above and illustrated in the accompanying Figures. Therefore, the description above should not be considered as a limitation, but merely as an illustration of the various embodiments. Those skilled in the art could consider other modifications within the scope and spirit of the appended claims. Furthermore, each above-mentioned patent is incorporated by reference in its entirety.

The invention claimed is:

1. A method for measuring the displacements of a vertebral column, the vertebral column having a segment comprising at least one vertebra, each vertebra in the segment having a body delimited by an upper vertebral end plate and a lower vertebral end plate, the method comprising:
providing a location marker attached to each vertebra in the segment,
detecting an initial orientation of each location marker by a location system, in a global reference frame,
determining an initial vector for each vertebra in the segment, in the global reference frame, the initial vector being normal to a vertebral plane of the vertebra, the vertebral plane being parallel to at least one of the upper vertebral end plate and the lower vertebral end plate of the vertebra,
calculating a geometric transformation for each vertebra, the geometric transformation representing relative orientation of the initial vector with respect to the initial orientation, the geometric transformation comprising rotation and translation transformations,
measuring a displacement of at least one vertebra in the segment, comprising:
detecting a current orientation of the location marker attached to the at least one vertebra, in the global reference frame,
calculating a current vector of the at least one vertebra in the global reference frame, the current vector being normal to the vertebral plane of the at least one vertebra, calculating the current vector being performed from the current orientation and the geometrical transformation of the at least one vertebra, and
calculating an angle between the current vector of the at least one vertebra and a current vector of another vertebra in the segment.

2. Method according to claim 1, comprising, after calculating a geometric transformation for each vertebra:
selecting a reference vertebra among the vertebrae in the segment, the reference vertebra having a reference plane, and
calculating, for each vertebra in the segment, an angle between the reference plane and the vertebral plane of each vertebra in the segment, and
displaying the angles calculated.

3. Method according to claim 1, comprising:
calculating the current vector of the at least one vertebra and the current vector of other vertebrae in the segment,
calculating an angle between the current vector of the at least one vertebra and the current vector of each of the other vertebrae in the segment, and
displaying the angles calculated.

4. Method according to claim 1, comprising, after calculating the geometric transformation associated for each vertebra:
selecting a reference vertebra among the vertebrae in the segment, the reference vertebra having a reference plane corresponding to the vertebral plane, and
projecting each current vector of each vertebra in the segment to said at least one reference plane,
calculating angles between the projected current vectors, and
displaying the angles calculated.

5. Method according to claim 1, wherein determining the initial vector for each vertebra in the segment comprises:
providing an instrument having a portion, the instrument providing an orientation vector for the portion, positioning the portion of the instrument in a first position included in the vertebral plane of each vertebra, the instrument providing a first orientation vector included in each vertebral plane, and positioning the portion of the instrument in a second position included in the vertebral plane of each vertebra, the instrument providing a second orientation vector included in each vertebral plane, determining the initial vector for each vertebra from the first and second orientation vectors provided for each vertebra.

6. Method according to claim 5, wherein the portion of the instrument comprises a rod opaque to X-rays, and the instrument provides an orientation vector corresponding to a longitudinal direction of the rod, and wherein determining the initial vector for each vertebra in the segment comprises:

providing an X-ray emitter and a detector for generating a radiographic X-ray picture of the vertebrae in the segment and the rod, displaying a radiographic X-ray picture of a vertebra and the rod for each vertebra in the segment, positioning the X-ray emitter and the detector perpendicularly to the segment so that the at least one end plate of the vertebra is represented by a line in the radiographic X-ray picture, and wherein when positioning the portion of the instrument in the first and second positions, the opaque rod is represented in the radiographic X-ray picture by a line parallel to the line representing said at least one end plate.

7. Method according to claim 6, wherein determining the initial vector for each vertebra in the segment comprises further comprises displaying a grid of reference lines in the radiographic X-ray picture, the reference lines being displayed parallel to each other and to the opaque rod of the instrument.

8. Method according to claim 6, wherein positioning the portion of the instrument in the first and second positions comprises positioning the rod against the detector.

9. Method according to claim 6, wherein determining the initial vector for each vertebra in the segment comprises calculating an orientation of the line representing said at least one end plate, an orientation of the line representing the rod, and an angle between said orientations of the lines.

10. Method according to claim 9, wherein determining the initial vector for each vertebra in the segment further comprises a step of displaying the angle between said orientations of the lines.

11. Method according to claim 9, wherein the initial vector normal to the vertebral plane of the vertebra in the segment is corrected from the angle between said orientations of the lines.

12. Method according to claim 5, wherein the instrument comprises at least one sensor, each sensor detecting a tissue and differentiating between a bone tissue and an intervertebral tissue, and when positioning the portion of the instrument in the first or the second position, said at least one sensor detects an intervertebral tissue.

13. Method according to claim 5, wherein the portion of the instrument is opaque to X-rays, and wherein determining the initial vector for each vertebra in the segment comprises:

providing an X-ray emitter and a detector for generating a radiographic X-ray picture of the vertebrae in the segment and the opaque portion, displaying a radiographic X-ray picture of the vertebra and the opaque portion for each vertebra, positioning the X-ray emitter and the detector perpendicularly to the segment so that the at least one end plate of the vertebra is represented by a line in the radiographic X-ray picture for each vertebra, positioning the portion of the instrument in the first or second positions comprising positioning the opaque portion to represent a line in the radiographic X-ray picture, and calculating an orientation of the line representing said at least one end plate, an orientation of the line representing the opaque portion, and calculating an angle between said orientations of the lines, correcting the initial vector from the angle calculated.

14. Method according to claim 1, wherein determining the initial vector for each vertebra in the segment comprises:

providing an instrument having a portion, the instrument providing an orientation vector for the portion to the location system, positioning the portion of the instrument in a first position included in the vertebral plane for each vertebra, the instrument providing a first orientation vector included in each vertebral plane, and positioning the portion of the instrument in a second position included in a plane perpendicular to the vertebral plane for each vertebra, the instrument providing a second orientation vector included in the perpendicular plane, determining the initial vector for each vertebra from the first and second orientation vectors provided for each vertebra.

15. Method according to claim 1, wherein determining the initial vector for each vertebra in the segment comprises:

providing an instrument having a portion, the instrument providing an orientation vector perpendicular to the portion, positioning the portion of the instrument in a first position included in the vertebral plane for each vertebra, the instrument providing a first orientation vector perpendicular to each vertebral plane, and determining the initial vector for each vertebra from the first orientation vector provided for each vertebra.

16. Method according to claim 15, wherein the portion of the instrument is a plate.

17. Method according to claim 16, wherein the plate is opaque to X-rays, and wherein determining the initial vector for each vertebra in the segment comprises:

providing an X-ray emitter and a detector for generating a radiographic X-ray picture of the vertebrae in the segment and the plate, displaying a radiographic X-ray picture of the vertebra and the plate for each vertebra, positioning the X-ray emitter and the detector perpendicularly to the segment so that the at least one end plate of the vertebra is represented by a line in the radiographic X-ray picture for each vertebra in the segment, and wherein when positioning the portion of the instrument in the first position, the plate is positioned to represent a line parallel to the line representing said at least one end plate in the radiographic X-ray picture.

18. Method according to claim 15, wherein the instrument comprises at least one sensor, each sensor detecting a tissue and differentiating between a bone tissue and an intervertebral tissue, and when positioning the portion of the instrument in the first position, said at least one sensor detects an intervertebral tissue.

19. Method according to claim 1, comprising an instrument with at least one set of at least two sensors, each sensor detecting a tissue and differentiating between a bone tissue and an intervertebral tissue, the instrument being provided with a location marker providing the location system with an orientation vector perpendicular to a detection plane formed by said at least two sensors, and wherein determining the initial vector comprises:

positioning said at least two sensors to detect an intervertebral tissue, the instrument providing an orientation vector, determining the initial vector from the orientation vector.

20. Method according to claim 19, wherein the instrument comprises a first set of at least two sensors, and a second set of at least two sensors, wherein the orientation vector is perpendicular to detection planes respectively formed by the first and second sets of at least two sensors, and comprising positioning the first and second sets of at least two sensors to detect two different tissues.

21. Method according to claim 1, wherein determining the initial vector in the segment for each vertebra comprises:

providing an instrument provided with a portion opaque to X-rays, an X-ray emitter and a detector for generating a radiographic X-ray picture of the vertebrae in the segment and the opaque portion, the opaque portion being movably mounted on the detector, and the instrument being further provided with a location marker providing an orientation vector of the opaque portion and a vector normal to a plane of the detector, positioning the X-ray emitter and the detector perpendicularly to the segment so that at least one end plate of the vertebra is represented by a line in the radiographic X-ray picture for each vertebra, and positioning the opaque portion of the instrument to represent in the radiographic X-ray picture at least one line parallel to the line representing said at least one end plate, determining the initial vector from the vector normal to the plane of the detector and the orientation vector of the opaque portion.

22. A method for measuring the displacements of a vertebral column, the vertebral column having a segment comprising at least one vertebra, each vertebra in the segment having a body delimited by an upper vertebral end plate and a lower vertebral end plate, the method comprising:

providing a location marker attached to each vertebra in the segment, providing a location system configured to detect, in a global reference frame, orientations of each location marker, an initial step, for each vertebra in the segment, comprising:

a detection by the location system, in the global reference frame, of an initial orientation of the location marker associated with the vertebra in the segment, a determination by the location system, in the global reference frame, of an initial vector normal to a vertebral plane parallel to at least one end plate of the vertebra in the segment, and a calculation by the location system of a geometric transformation associated with the vertebra in the segment comprising rotation and translation transformations to calculate the initial vector normal to the vertebral plane of the vertebra in the segment relative to that of the initial orientation of the associated location marker, the method further comprising:

a step of measuring a displacement of at least one vertebra in the segment, comprising:

a detection by the location system, in the global reference frame, of the current orientation of the location marker associated with said at least one vertebra in the segment, and a calculation by the location system, in the global reference frame, of the current vector normal to the vertebral plane of said at least one vertebra in the segment from the current orientation of the location marker associated and the geometrical transformation associated with said at least one vertebra, calculating and displaying angles between the current vector of the at least one vertebra and the current vector of each of other vertebrae of the segment, and a step of correcting a balance of the vertebral column during a surgical procedure.

* * * * *